(12) United States Patent
Steikuniene et al.

(10) Patent No.: US 10,993,625 B1
(45) Date of Patent: May 4, 2021

(54) SYSTEM, METHOD, AND APPARATUS FOR TEMPERATURE ASYMMETRY MEASUREMENT OF BODY PARTS

(71) Applicant: UAB Diabetis, Vilnius (LT)

(72) Inventors: Urte Steikuniene, Vilnius (LT); Gintare Marine, Vilnius (LT); Rytis Zajanckauskas, Vilnius (LT); Jonas Guzaitis, Kaunas (LT)

(73) Assignee: UAB DIABETIS, Vilnius (LT)

( * ) Notice: Subject to any disclaimer, the term of this patent is extended or adjusted under 35 U.S.C. 154(b) by 0 days.

(21) Appl. No.: 16/849,702

(22) Filed: Apr. 15, 2020

Related U.S. Application Data

(63) Continuation of application No. 16/646,103, filed as application No. PCT/IB2020/051950 on Mar. 6, 2020.

(51) Int. Cl.
 *A61B 5/01* (2006.01)
 *A61B 5/00* (2006.01)

(52) U.S. Cl.
 CPC .............. *A61B 5/015* (2013.01); *A61B 5/004* (2013.01); *A61B 5/0008* (2013.01); *A61B 5/0013* (2013.01); *A61B 5/0035* (2013.01); *A61B 5/0075* (2013.01); *A61B 5/0077* (2013.01); *A61B 5/6898* (2013.01); *A61B 2562/0233* (2013.01); *A61B 2576/02* (2013.01)

(58) Field of Classification Search
 None
 See application file for complete search history.

(56) References Cited

U.S. PATENT DOCUMENTS

| | | | | |
|---|---|---|---|---|
| 7,924,312 | B2 * | 4/2011 | Packard | G06T 7/136 348/164 |
| 2013/0261494 | A1 * | 10/2013 | Bloom | A61B 5/0075 600/549 |
| 2013/0261495 | A1 * | 10/2013 | Linders | A61B 5/6892 600/549 |
| 2013/0261496 | A1 * | 10/2013 | Engler | A61B 5/0022 600/549 |
| 2015/0057562 | A1 * | 2/2015 | Linders | A43B 3/0005 600/549 |
| 2015/0190059 | A1 * | 7/2015 | Petersen | G16H 50/30 600/474 |

(Continued)

*Primary Examiner* — Angela M Hoffa
*Assistant Examiner* — Younhee Choi

(57) ABSTRACT

Method for automatic detection of inflammation or functional disorder according to temperature asymmetry estimation in contralateral body parts is presented. Simultaneously recorded thermogram and the optical image of the inspected and contralateral body parts are sent to the processing unit, where they are stored, processed, and analyzed. Method automatically detects outlines of body parts in thermograms and optical images. Grid of points of interest is distributed inside the inspected and the contralateral body part's outline. Temperature maps are calculated according to both grids points and the temperature disparity map is estimated. The set of inflammation regions is obtained by analyzing the temperature disparity map and collecting adjacent points containing temperature differences surpassing the threshold. This is non-invasive and non-contact inspection method, suitable for real world environments with natural home or health care institutions background.

12 Claims, 5 Drawing Sheets

(56) References Cited

U.S. PATENT DOCUMENTS

| | | | |
|---|---|---|---|
| 2016/0100790 A1* | 4/2016 | Cantu | A61B 5/0064 600/306 |
| 2016/0150976 A1* | 6/2016 | Fang | A61B 5/0077 600/474 |
| 2016/0183879 A1* | 6/2016 | Goldish | A61B 5/447 600/474 |
| 2016/0192844 A1* | 7/2016 | Linders | A61B 5/0075 600/549 |
| 2016/0256056 A1* | 9/2016 | Petersen | G16H 50/20 |
| 2017/0127999 A1* | 5/2017 | Linders | A61B 5/742 |
| 2018/0132726 A1* | 5/2018 | Dickie | G01S 17/86 |
| 2020/0113510 A1* | 4/2020 | Linders | A61B 5/015 |
| 2020/0121245 A1* | 4/2020 | Barclay | A61B 5/445 |

* cited by examiner

SYSTEM, METHOD, AND APPARATUS FOR TEMPERATURE ASYMMETRY MEASUREMENT OF BODY PARTS

CROSS REFERENCE TO RELATED APPLICATION

This application is a continuation of U.S. application Ser. No. 16/646,103 entitled SYSTEM, METHOD, AND APPARATUS FOR TEMPERATURE ASYMMETRY MEASUREMENT OF BODY PARTS, filed on Mar. 10, 2020, which is hereby incorporated by reference in its entirety.

FIELD OF THE INVENTION

The invention generally relates to medical infrared thermal imaging methods and, more particularly, the invention relates to the method for automatic temperature asymmetry estimation.

DISCUSSION OF BACKGROUND ART

During everyday conditions, a body temperature of a person is higher than ambient temperature. With certain techniques, such as infrared thermal imaging, temperature maps of human or other animal body parts could be obtained. When some disease or functional change of person body arises at a specific area, the temperature of the affected body part of the human or other animal could change significantly compared with normal tissue. Inflammation, pre-cancerous tissue formation, tumor growths, or other factors could increase the temperature, while diseases such as vasculitis or artery sclerosis could decrease the temperature of the affected body part.

For example, diabetic foot wounds, or diabetic foot ulcers (DFUs) are among the most common foot complications that critically affect about 15% of the diabetic population. The risk factors leading to the development of foot ulcers are primarily neuropathy and arterial disease in the lower limbs. For diabetic persons with neuropathy, DFUs may develop after minor wounds or skin lesions on the lower limb. DFUs are difficult to diagnose early, and even more difficult to treat. Delayed diagnosis, treatment, and other factors may contribute to further complications of the ulcer, which often lead to the need for surgical interventions and even amputations. Evaluation of DFU requires a multidisciplinary foot care team. Such evaluation may include the medical history of the human or animal, laboratory test results, and dermatological, musculoskeletal, neurological and vascular status. Self-inspection of the feet is an important part in detecting diabetic complications in early stages, but this is often impeded by health impairments related to diabetes and other comorbidities, such as eyesight, limited mobility, or social impairments. An alternative to self-evaluation is frequent examination by health professionals, but this is costly, time-consuming, and not a common option for many people. Thus, an advanced home assessment tool to monitor the feet of people with diabetes is needed. Numerous studies have indicated that a localized temperature change in the foot is a clear precursor to a diabetic foot ulcer. However, the temperature differences for DFU regions are small, challenging to monitor, and difficult to determine using analogue means, and are not widely monitored in current medical practice for DFU diagnosis.

The infrared thermal imaging is a preferable and useful way to record temperature maps because it is a non-invasive and non-contact technology that acquires thermal images based on the emitted heat (thermal energy) from the body. Thermal radiation is electromagnetic waves from the Long Wavelength Infrared (LWIR) range 0.000314 inches to 0.000551 inches (8 micrometers (8 pin) to 14 pin)). The infrared techniques allow rapid capturing of large number of pixels or picture elements. The individual pixels at the respective points denote the local temperature, and the collection of these pixels create an image illustrating the surface temperature distribution. Infrared thermal imaging has made it possible to measure any increased temperature that occurs in some regions within the foot. It was determined that a 1.8 degree Fahrenheit (1.8° F.) to 3.6° F. (1° Celsius (c) to 2° C.) temperature increase within the foot, compared to the contralateral foot's mean temperature requires an accurate assessment in order to decide whether it is a normal increase or an occurrence of foot ulcers. Moreover, temperature differences of more than 3.96° F. (2.2° C.) between a region on one foot and the same region on the contralateral foot are considered hyperthermia. Monitoring such differences through thermal images captured with the use of infrared thermography devices proved to be an efficient way of detecting diabetic foot ulceration.

Patent document US20100191124A1 (application filing date of 2008 Apr. 15) provides a system and a method for using three-dimensional infrared imaging to provide psychological maps of individuals. Calibrated infrared and range imaging sensors are used to produce a true-metric three-dimensional (3D) surface model of any region of the body within the fields of view of both sensors. Curvilinear surface features in both modalities are caused by internal and external anatomical elements. Features are classified by origin, location, and characteristics to produce annotations that are recorded with the images and feature maps in reference image libraries. However, the method is not sensitive enough to detect minor changes in person's body temperature, such as inflammation or diabetic foot ulceration. Also, the method does not use both left and right feet, arms or other body parts temperature data values for comparing the temperature differences. Therefore, it is not suitable for detecting inflammation, diseases or functional disorders.

Patent document US20190021649A1 (application fling date 2017 Jul. 24) describes a medical diagnostic apparatus, comprising a controller; a user interface configured for user interaction with the medical diagnostic apparatus; a platform comprising a horizontal surface, wherein at least a portion of the horizontal surface is transparent to visible light; a weight measurement system coupled to the platform; and at least one visible light image sensor positioned below the horizontal surface that is capable of producing a diagnostic visible light image of a bottom portion of a foot or feet positioned on the horizontal surface. The document also provides a method for automated diagnosis of a diabetic foot condition, where the method comprises capturing optical image data of a target area of a foot; collecting, by a touch sensitivity testing device of the medical diagnostic apparatus, physical touch sensitivity data for the target area of the foot; transmitting, by the medical diagnostic apparatus, the optical image data, the physical touch sensitivity data, or a combination of such data to an analysis engine; and outputting, by the analysis engine, one or more indications of a diabetic foot condition. However, the medical diagnostic apparatus uses optical image data and the determination of foot conditions data is collected by contact of feet with the platform. Even if the apparatus could comprise at least one infrared image sensor, the infrared imaging makes only a supplementary role, the infrared imaging quality is not developed in detail. Moreover, the differences of the temperature due to the functional disorders are small, and the problems of an infrared spatial resolution and the determination of a body part outline is not solved at all.

Current technologies, which use non-contact thermal imaging of the person's body parts for detection of inflammation, do not have an automatic way of distinguishing the person's body parts outline from the surrounding background. They use such solutions as covering non-monitored person's body parts with a damp cold towel, placing the person in a large box, etc. Existing methods don't allow to monitor and detect inflammation, diseases or functional disorders which have slightly increased local temperature maps.

Therefore, there is a need for a system, method, and apparatus, whereby:
- optical and thermal imaging could be performed simultaneously;
- thermal imaging of both left and right body parts could be performed simultaneously;
- the method could automatically evaluate the presence of an inflammation or functional disorder, inform the person and make recommendations;
- the outline of person's body parts could be detected automatically;
- exact comparison between slightly different (assymetric) body part outlines could be performed;
- the exact area of an inflammation or functional disorder could be mapped;
- small changes in the body part temperature could be detected;
- the apparatus should be non-invasive, non-contact, portable, and could be used both at home or at a clinical institution;
- the apparatus should have a database of stored thermograms, which could be viewed distantly by healthcare professionals or the administrator;

The present disclosure describes a system, an apparatus, a new method, and uses of the system, apparatus, and method which satisfy the above mentioned requirements.

SUMMARY OF THE INVENTION

A system, method, apparatus, and use of the system, method, and apparatus are presented, which automatically detects regions of inflammation or functional disorder according to temperature asymmetry estimation in contralateral body parts. This is a non-invasive and non-contact body part inspection method. The method could be used to determine the inflammation or functional disorder regions between contralateral body parts or adjacent areas of a human or other animal. Simultaneously recorded thermogram and the optical image of the inspected and contralateral body parts are sent to the processing unit, where they are stored, processed and analyzed. The method automatically detects outlines of body parts in at least one thermogram and at least one optical image. Grid of points of interest are distributed inside the inspected outline of the body part, and the same grid with applied geometrical transformations is distributed inside the contralateral body part outline. Temperature maps are calculated according to both grids points and a temperature disparity map is estimated by subtracting the appropriate temperature values of inspected and contralateral temperature maps of the body parts. The set of inflammation regions is obtained by analyzing the temperature disparity map and collecting adjacent points containing temperature differences that surpass the threshold. The exact areas of inflammations are determined. Thus, the early onset of the disease or pre-disease state could be detected. The method could be used both at home and at healthcare institutions. There is no need to use any precautions (such as damp cold towel or screen) for background elimination. The method is capable of determining an outline of a body part in real world environments with natural home or health care institution backgrounds, which may include other objects that emit thermal radiation.

Disclosed herein is a method for detection of a health disorder based on temperature asymmetry estimation in contralateral or reference body parts. The method includes recording, using an optical camera and a thermal camera, an optical image and a thermogram corresponding to an inspected body part and a reference or contralateral body part; receiving, by a processing unit, the optical image and the thermogram; estimating, by the processing unit, a recorded image displacement based on the thermogram and the optical image; and determining, by the processing unit, that a functional disorder or inflammation of the inspected body part has occurred by comparing the thermogram corresponding to the inspected body part to the thermogram corresponding to the reference or contralateral body part based on the recorded image displacement.

In any of the foregoing embodiments, estimating the recorded image displacement includes localizing a template of the inspected body part by locating corresponding pairs of keypoints in the optical image and in the thermogram, and calculating a nonconformity error between the corresponding pairs of keypoints in the optical image and in the thermogram.

In any of the foregoing embodiments, estimating the recorded image displacement further includes fine tuning by fitting a shape of the inspected body part on the thermogram and the optical image.

In any of the foregoing embodiments, estimating the recorded image displacement further includes localizing a reference template of the reference or contralateral body part by locating corresponding pairs of reference keypoints in the optical image and in the thermogram, and calculating a nonconformity error between the corresponding pairs of reference keypoints in the optical image and in the thermogram.

In any of the foregoing embodiments, estimating the recorded image displacement further includes fine tuning by fitting a reference shape of the reference or contralateral body part on the thermogram and the optical image.

In any of the foregoing embodiments, the thermogram and the optical image are recorded simultaneously.

In any of the foregoing embodiments, determining that the functional disorder or inflammation of the inspected body part has occurred includes rejecting non-confident inflammation or functional disorder regions.

In any of the foregoing embodiments, determining that the functional disorder or inflammation of the inspected body part has occurred includes estimating temperature maps for the inspected body part and the reference or contralateral body part based on the thermogram of the inspected body part and based on the thermogram of the reference or contralateral body part.

In any of the foregoing embodiments, comparing the thermogram corresponding to the inspected body part to the thermogram corresponding to the reference or contralateral body part includes comparing the estimated temperature maps.

In any of the foregoing embodiments, the inspected body part is a foot and the functional disorder or inflammation includes early detection of a diabetic foot ulcer.

In any of the foregoing embodiments, the inspected body part is a breast and the functional disorder or inflammation includes early detection of pre-cancerous breast tissue.

Also disclosed is a system for detection of a health disorder based on temperature asymmetry estimation in contralateral or reference body parts. The system includes a stand configured to rest on a surface and having a body part rest support configured to support an inspected body part; an optical camera configured to detect image data corresponding to an inspected body part and a reference or contralateral body part, the optical camera further configured to be coupled to the stand; a thermal camera configured to detect a thermogram corresponding to the inspected body part and the reference or contralateral body part, the thermal camera further configured to be coupled to the stand; and a processor configured to receive the image data and the thermogram and to determine that a functional disorder or inflammation of the inspected body part has occurred by comparing the thermogram corresponding to the inspected body part to the thermogram corresponding to the reference or contralateral body part.

In any of the foregoing embodiments, the processor is further configured to estimate a recorded image displacement based on the thermogram and the optical image, and to determine that the functional disorder or inflammation has occurred based on the recorded image displacement.

In any of the foregoing embodiments, estimating the recorded image displacement includes localizing a template of the inspected body part by locating corresponding pairs of keypoints in the optical image and in the thermogram, and calculating a nonconformity error between the corresponding pairs of keypoints in the optical image and in the thermogram.

In any of the foregoing embodiments, the optical camera and the thermal camera are located on a mobile device, and the stand is configured to support the mobile device to direct the optical camera and the mobile camera towards the body part rest support.

In any of the foregoing embodiments, the mobile device further includes a network access device configured to transmit the thermogram and the optical image to the processor.

In any of the foregoing embodiments, the mobile device further includes a display configured to output data indicating that the functional disorder or inflammation of the inspected body part has occurred.

Any of the foregoing embodiments may further include a network access device configured to transmit data indicating that the functional disorder or inflammation of the inspected body part has occurred to a remote device associated with a healthcare worker.

Also disclosed is an apparatus for detection of a health disorder based on temperature asymmetry estimation in contralateral or reference body parts. The apparatus includes a base configured to rest on a surface; at least one camera holder configured to fix and support an optical camera and a thermal camera; a mobile device holder configured to support a mobile device; and a body part rest support configured to support an inspected body part and a reference or contralateral body part in such a location in which the optical camera and the thermal camera can capture image data and a thermogram, respectively, of the inspected body part and the reference body part.

Any of the foregoing embodiments may further include a processing unit configured to receive the image data and the thermogram and to determine that a functional disorder or inflammation of the inspected body part has occurred by comparing the thermogram corresponding to the inspected body part to the thermogram corresponding to the reference or contralateral body part.

In any of the foregoing embodiments, the processing unit includes: a processing unit control system configured to communicate with the mobile device; a database configured to store optical and thermal images and user account information; and a processor coupled to the processing unit and the database and to perform computing, analysis, and comparison of the optical image and the thermogram.

DETAILED DESCRIPTION OF THE INVENTION

Figure 1:
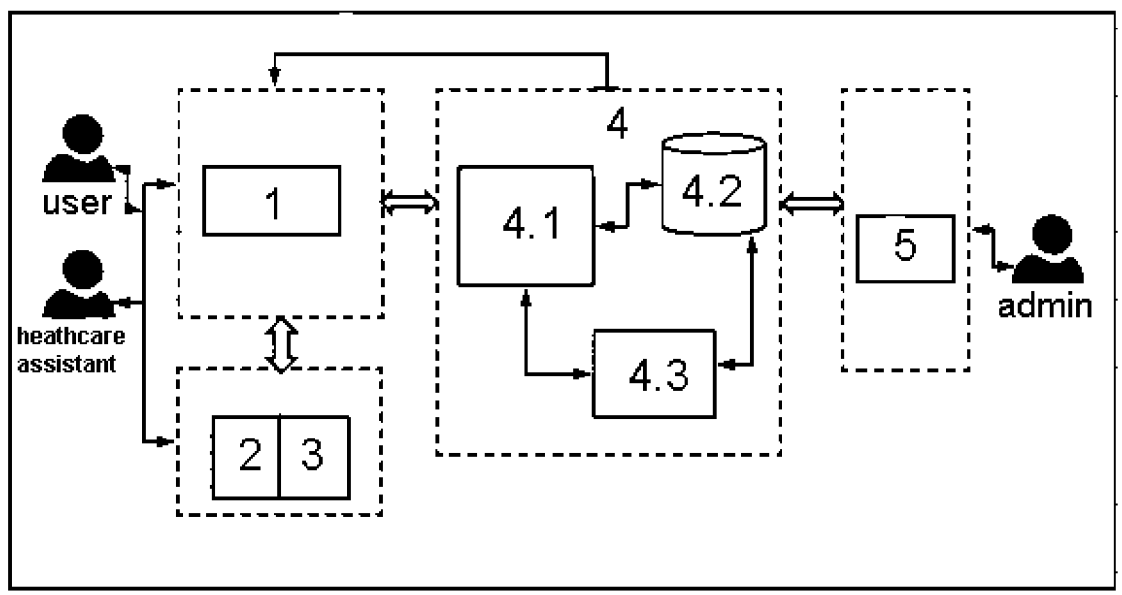
FIG. 1. A block diagram depicting principle components of the present invention. There 1—mobile device, 2—optical camera, 3—thermal camera, 4—processing unit, 5—admin output device.

The method for automatic detection of an outline of body parts of a human or animal and evaluation of temperature maps is implemented by using the apparatus, presented in FIG. 1. The apparatus receives thermal and optical images from body parts and determines the outline of the body parts and the temperature data values regardless of the natural background. The apparatus forms thermal maps of the outlines of the body part in the thermograms, makes a comparison between inspected and contralateral thermal maps, and determines whether the thermal difference map presents at least one of an indicative inflammation pattern or a functional disorder. Finally, the apparatus produces an output message indicating whether the thermal difference map noted a significant increase of temperature in one or several areas on the inspected body parts. In other words, the risk of disease emerges as a function of whether the temperature map presents at least one prescribed pattern indicative of inflammation or functional disorder. The apparatus can be used by a person at home or at a health care institution.

The following terms, which are used with regard to the description of the apparatus and the method, are defined as follows:

Optical image—a two-dimensional or three-dimensional digital image composing color values in each point or pixel. Optical image creation is accomplished using an optical camera. It is desirable for the optical image and the thermogram to be taken at the same moment in time.

Thermogram—a two-dimensional or three-dimensional digital image composing temperature values in each point. Thermogram creation is accomplished using a thermal camera. It is desirable for the optical image and the thermogram to be taken at the same moment in time. In that regard, it is desirable for the optical image and the thermogram to be taken at exactly the same time, within 0.1 seconds of each other, with 0.5 seconds of each other, within 1 second of each other, within 5 seconds of each other, or the like.

Inspected body part—a body part of a human or animal that is being examined; the optical and thermal images are being taken of the inspected body part.

Contralateral body part—contralateral part to the inspected body part, which is used as a reference for the temperature maps and for the temperature difference estimation between inspected and contralateral body parts. If the unpaired body part is monitored, the contralateral body part is an adjacent area to the inspected body part. The same inspected body part can be used as a reference when the data is used from a different optical image or a different thermogram which was taken previously.

Body part template—non-self-intersecting closed polygon of a fixed amount of points, replicating a body part outline. The body part template may have additional points to mark points-of-interest inside the body part outline. For example, if the body part is a foot, additional points to mark could be points between the toes. Such points are not connected with the main template polygon and can be used to refine non-affine transformation.

Base body part template—the body part template statistically closest to a body part.

Set of points of interest—a set of points laid out inside the body part template polygon. Such points are used to define locations of the temperature measurements while calculating temperature disparity maps. Coordinates of points may be defined in Cartesian, Polar, or any other coordinate system capable of defining the location of a point on an optical image or a thermogram.

Point distribution—may include a regular point distribution (e.g. grid) or an irregular point distribution (e.g. concentrating points near the most vulnerable areas of the body part of the human or animal).

Base set of points of interest—a set of points laid out inside the base body part template polygon. Locations of such points are used to estimate the locations of a set of points of interest by applying affine and non-affine transformations of a body part template.

Temperature map—a set of temperature values, which composes generalized temperature values estimated from the thermogram locations defined by the appropriate points of interest. The size of the temperature map is equal to the size of a set of points of interest used to create the temperature map.

Temperature disparity maps—a set of temperature values obtained while subtracting the temperature values in a temperature map of a contralateral body part from the appropriate temperature values in a temperature map of the inspected body part.

Keypoints—spatial locations in the thermogram and the optical image, which marks highly-distinctive locations of the captured objects.

Inflammation or functional disorder region—a set of points composing the temperature disparity values higher than the medically-based threshold.

The method, described in the present disclosure, identifies the outline of body parts of a human or animal. The method is based on monitoring contralateral body parts or adjacent areas of a body part, taking thermal and optical images, sending signals with these images to the processing unit, and processing the signals at the processing unit. The method could be used with the system or apparatus, which is based on taking thermal and optical images of contralateral body parts in a 'mirror image,' taking images from the contralateral body parts such as left and right feet, legs, arms, breasts, or other. If the body part does not have a contralateral part, images from adjacent areas of the body part are taken. The system or apparatus comprises the following components (FIG. 1):

Mobile device (1);
Optical camera (2);
Thermal camera (3);
Processing unit (4).

The apparatus optionally could have an admin output device (5) and a stand (6).

A mobile device (1) may include a mobile telephone, tablet, laptop or other computing device, which has a central processing unit (which may include a processor, controller, or other physical hardware that implements logic); a storage unit (which may include any non-transitory memory); a battery; a touchscreen or a monitor; input means, such as digital or physical keyboard or means for accepting voice commands; output means (such as a speaker, light source, display, or the like); connections (such as a port or other connection capable of communicating via a wired or wireless protocol) to an optical camera (2) and/or a thermal camera (3) (in various embodiments, one or both of the optical camera (2) or the thermal camera (3) may be incorporated into the mobile device (1)); connection means (such as a port or other connection capable of communicating via a wired or wireless protocol) to a processing unit (4) via a network access device (e.g., Wi-Fi, Bluetooth, cellular networks, near field communication, or the like). The mobile device (1) may include an integrated optical camera (2) and/or thermal camera (3). The mobile device (1), with the help of installed mobile device application, activates and configures the system or apparatus, controls the operation of the optical camera (2) and the thermal camera (3), receives thermal and optical image signals from the optical camera (2) and the thermal camera (3), stores, processes, and sends these signals to the processing unit (4). The mobile device (1) may be controlled by the user, which could be the person, his/her healthcare assistant, or the caregiver. In various embodiments, the mobile device (1) may be controlled automatically using an algorithm stored in the storage unit. For example, the mobile device (1) may be controlled to begin collecting images as soon as a known or recognized image is in the field of view of the camera (3). The user may be required or requested to create a password-protected account at his/her mobile device (1). Afterward the same account may be used by that user to collect and store his/her body parts images and other signals. In separate embodiments of the disclosure, the user may use the mobile device (1) without the user account. After the images are taken and sent to the processing unit, the mobile device (1) may receive feedback from the processing unit (4), which could be displayed on the screen as a text message, or via the loudspeaker as an audio message. The feedback informs the user about the health conditions of the body, based on the thermal and optical images. If a pattern indicative of inflammation or functional disorder is detected (e.g., a significant increase in temperature above a temperature difference threshold is detected in a portion of the body part), the recommendation will be provided to consult with the professional medical assistance for further investigation and treatment. In various embodiments, a description of the inflammation or functional disorder may be immediately provided to the user via the output device (e.g., display or speaker).

An optical camera (2) may include an optical instrument used to record still or moving images. The optical camera (2) consists of a lens which focuses reflected light from the body part of a human or animal, an image recording mechanism, and a camera body which holds the image recording mechanism. The optical camera (2) could be a separate mechanism, or an integral part of the mobile device (1). The optical camera (2) may be connected to the mobile device (1) via a network access device (e.g., USB, lightning plug-in cable, or by any other conventional or proprietary means). The optical images may be stored in a digital form at the physical medium of the optical camera (2) itself, in the mobile device (1), or in the processing unit (4) (FIG. 1).

A thermal camera (3) may include an optical instrument, which creates still or moving images using infrared radiation in the Long Wavelength Infrared (LWIR) range 0.000315 inches to 0.000551 inches (8 micrometers (μm) to 14 μm). The thermal camera (3) may include a thermal image sensor, an image recording mechanism, and a camera body which holds the image recording mechanism. The thermal camera (3) could be a separate mechanism, or an integral part of the mobile device (1). The optical camera (2) and the thermal camera (3) may be two separate mechanisms, may be incorporated into a single device, or may be an integral part of the mobile device (1). The thermal camera (3) may be connected to the mobile device (1) via a network access device (e.g., USB, lightning plug-in cable, or by other conventional or proprietary means). The thermal camera (3) creates images, which are called thermograms. Thermograms could be stored in a digital form at the physical medium of the thermal camera (3) itself, in the mobile device (1), or in the processing unit (4) (FIG. 1).

A processing unit (4) is a computer or a network of computers that communicate with the mobile device (1) and an admin output device (5) through the internet, local intranet network, directly, or via any other means. In that regard, the processing unit 4 may include a non-transitory memory, one or more processor, and a network access device capable of communicating via any known or other protocol (e.g., Wi-Fi, Bluetooth, NFC, lightening cable, USB cable, or the like) The processing unit (4) could be implemented on a single computer, on several computers connected in a network (e.g., a distributed processing system), or with many virtual machines in a cloud infrastructure. The processing unit (4) receives thermal and optical image signals from the mobile device (1), stores, analyses, and compares these signals, and sends the feedback to the mobile device (1) or to the admin output device (5). The processing unit (4) may include the following components (FIG. 1):

Processing unit control system (4.1);
Database (4.2);
Computing machine (4.3).

The processing unit control system (4.1) may include standard processing unit components, such as a motherboard, a processor, hard drives, a power supply, a network connection and others. In various embodiments, the processing unit control system (4.1) may include specialized hardware and/or software capable of performing the functions described herein relating to processing of the images and thermograms. The processing unit control system (4.1) is connected to a database (4.2) (which may include any non-transitory memory), a computing machine (4.3) of the processing unit (4), the mobile device (1), and the admin output device (5) outside the processing unit (4). The processing unit control system (4.1) is may be utilized for proper functioning of the processing unit (4) and for connecting the processing unit (4) with the mobile device (1) or the admin output device (5).

A database (4.2) is part of the processing unit (4), which stores data, optical and thermal images, files, user account information, and other data. The database (4.2) may be connected to the processing unit control system (4.1) and the computing machine (4.3).

The computing machine (4.3) may be part of the processing unit (4), which is connected to the processing unit control system (4.1) and the database (4.2). The computing machine (4.3) performs computing functions, comparison of signals (such as images or thermograms), and analysis of the signals (such as optical and thermal images). The computing machine (4.3) may identify an outline of one or more body part of a human or animal, evaluate temperature differences, make an evaluation about the inflammation or functional disorder, and performs other functional steps, such as those described with respect to the proposed method. The computing machine (4.3) may use filtering technologies and advanced statistical models to perform some or all of its functions. In various embodiments, machine learning functionality (e.g., artificial intelligence) may be a part of this technology, but is not a necessity.

An admin output device (5) (or just an "admin device" (5)) is a device, connected to the processing unit (4), which is used to access data (signals) related to a patient and captured by the camera (2) or thermal camera (3) (and/or data analyzed by the computing machine (4.3)) by the third party, such as administrator. An admin output device (5) remotely retrieves the signals from the processing unit (4) and then presents the required data, such as using an output device (e.g., a speaker, a display, a touchscreen, or the like). An admin output device (5) may be used by the administrator or the authorized healthcare professional.

Figure 2:
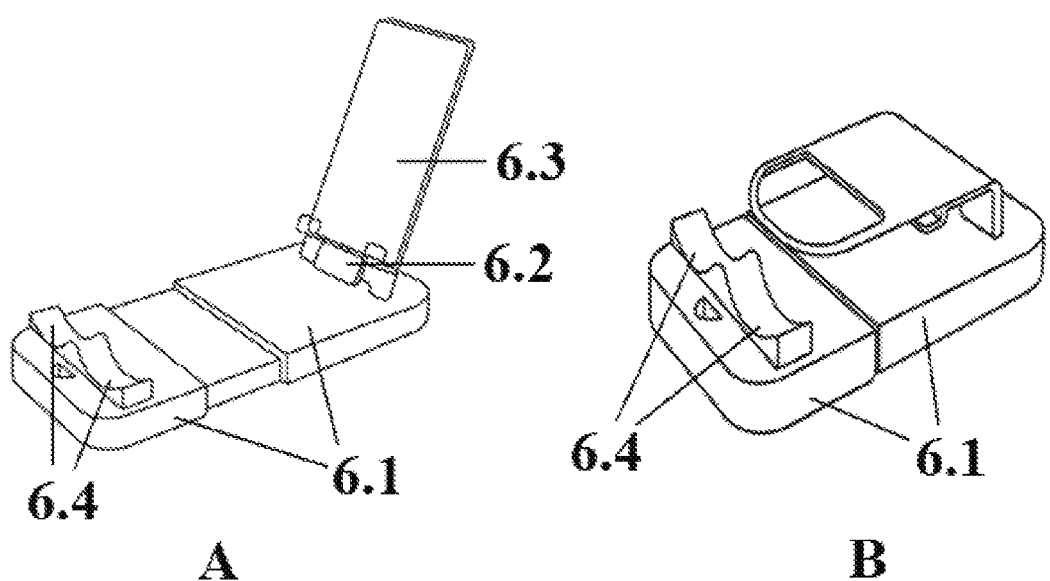
FIG. 2. Principle components of the stand (6). A—the stand (6) during operating conditions, B—the stand (6) when not in use. There 6.1—base of the stand, 6.2—cameras holders, 6.3—mobile device holder, 6.4—body parts rest support.

Referring now to FIGS. 1 and 2, a stand (6) is a device, which is used for placing and firmly fixing at least one of the mobile device (1), the optical camera (2), the thermal camera (3), and the body parts to be examined in the correct position for the inspection and/or the diagnosis. The stand (6) may be used by a person in order to self-inspect his/her body parts at home, or by his/her healthcare assistant at a healthcare institution. The stand (6) may be designed in a way that is suitable for people with limited mobility, has an attractive design, and has soft edges. The stand (6) comprises the following parts (FIG. 2A and FIG. 2B):

Base of the stand (6.1);
Cameras holders (6.2);
Mobile device holder (6.3);
Body parts rest support (6.4).

The base of the stand (6.1) is a part of the stand (6), which is used to firmly attach other parts of the stand (6) thereto. The base of the stand (6.1) may be made of one or more materials, such as metal, plastic, fiberglass, or the like. The size of the base (6.1) may be adapted to the size of the inspected body parts and the size of the mobile device (1), the optical camera (2) and the thermal camera (3) in such a way, that it would be easy to use and such that relatively high quality thermal and optical images may be achieved. In various embodiments, the components of the stand (6), such as the base of the stand (6.1) may be adjustable in order to compensate for users having different sized body parts. For example, the base of the stand (6.1) may have an adjustment mechanism that allows for easy and comfortable resting of a U.S. size 4 female foot and a U.S. size 16 male foot. The base of the stand (6.1) may include a hollow portion in the central part thereof in order to not obstruct optical and thermal images of the body parts. The base of the stand (6.1) may include a single unit, or it could be composed of several parts, which could be coupled together using any known technique (e.g., press-fit, fasteners, or the like). The base of the stand (6.1) is used for attaching the other parts of the stand (6) to a single device. When not in use, the base of the stand (6.1) can be partially pushed in (like a drawer) to take up less space (FIG. 2B). The base of the stand (6.1) is designed to rest on a surface such as a floor, a counter, or the like.

Cameras holders (6.2) are gadgets, which are attached to the Base of the stand (6.1). Cameras holders (6.2) may include adjustable fixing means in order to fix cameras of various sizes and configurations thereto, and may be designed to hold the optical camera (2) and/or the thermal camera (3) firmly fixed. Camera holders (6.2) may be an integral part of the stand (6), or they could be separate units, temporarily attached to the stand (6) with the help of the fixing means. In that regard, various camera holders (6.2) may be provided for holding cameras of various sizes and shapes. Camera holders (6.2) may be present at one side of the Base of the stand (6.1), opposite to a body parts rest support (6.4) (FIG. 2A and FIG. 2B). Camera holders (6.2) are used to fix and firmly hold the optical camera (2) and the thermal camera (3).

A mobile device holder (6.3) is a gadget, attached to the base of the stand (6.1), which has the adjustable fixing means in order to fix mobile devices of various sizes and configurations and holds the mobile device (1) firmly fixed. The mobile device holder (6.3) could be an integrate part of the stand (6), or it could be a separate unit, temporarily attached to the stand (6) with the help of a fixing means (such as a press-fit configuration, the use of fasteners, or the like). The mobile device holder (6.3) may be present besides the cameras' holders (6.2) and opposite to a body parts rest support (6.4) (FIG. 2A and FIG. 2B).

The body parts rest support (6.4) is a device, attached to the base of the stand (6.1), the form and size of which are adapted to comfortably and firmly hold the inspected person's body parts. The body parts rest support (6.4) could be an integrate part of the stand (6), or it could be one or more separate unit, temporarily attached to the stand (6) with the help of the fixing means (e.g., a press-fit configuration, the use of fasteners, or the like). The body parts rest support (6.4) may be present at that side of the Base of the stand (6.1) which is opposite to the camera's holders (6.2) and the mobile device holder (6.3). The body parts rest support (6.4) may be adjustable in order to support body parts of various shapes and sizes. For example, it may be adjustable to comfortably support a foot, a leg, an arm, a head, or any other body part. As another example, it may be adjustable to hold feet of all sizes, from a size 4 or below female foot to a size 16 or above male foot.

The method, described in the present disclosure, employs the above-mentioned system or apparatus for automatic detection of an outline of body parts and the evaluation of temperature maps. The method may include the following functional steps, but is not necessarily limited to all of the steps, and other steps may further be contemplated:

Recording of the thermograms and the optical images and sending them to the processing unit (4);
   Estimation of recorded image displacement in the thermogram and the optical image;
   Localization of inspected body part template considering body part outline in the thermogram and the optical image;
   Fine tuning of inspected body part template considering the body part outline in the thermogram and the optical image;
   Localization of contralateral body part template considering the body part outline in the thermogram and the optical image;
   Fine tuning of contralateral body part template considering the body part outline in the thermogram and the optical image;
   Estimation of sets of points of interest for both inspected body part and contralateral body part according the appropriate body part template;
   Estimation of temperature maps for both the inspected body part and the contralateral body part according to the appropriate set of points of interest;
   Estimation of temperature disparity map;
   Composition of set of inflammation or functional disorder regions;
   Analysis of inflammation or functional disorder regions;
   Detection of inflammation or functional disorder;
   Sending the user health state evaluation to the mobile device (1). Recording of the thermograms and the optical images and sending them to the processing unit (4)

The user may begin by connecting all the required components of the system or apparatus, register or login to his/her account using the mobile device (1), and prepare the mobile device (1) for controlling the apparatus. The user may then activate the optical camera (2) and the thermal camera (3) through the mobile device (1). The user may control the system or apparatus to begin collecting the optical images and thermograms using the mobile device (1) or a remote device. In various embodiments, the system or apparatus may begin collecting the optical images and thermograms as soon as the optical images or thermograms indicate that the body part(s) is in the correct location relative to the camera (2) and/or thermal camera (3). In various embodiments, both the optical image and the thermogram may be recorded simultaneously (e.g., at the same time, within 0.1 seconds of each other, within 0.5 seconds of each other, within 1 second of each other, or the like). In various embodiments, the optical image and the thermogram may be taken seconds (or up to a minute or more apart) so long as the body part remains in the same position. The optical images and the thermograms of the inspected and contralateral body parts may be recorded simultaneously or sequentially (with either optical images or thermograms recorded first). The recorded optical images and the thermograms could be stored in the mobile device (1) or could be send to the processing unit (4) without storing them in the mobile device (1) At the processing unit (4), the processing unit control system (4.1) receives the optical images and the thermograms and stores them at the database (4.2). Upon request, the optical images and the thermograms are retrieved from the database (4.2) and are processed by the computing machine (4.3). In various embodiments, machine learning may be used for processing the optical images and the thermograms. Use of machine learning may provide faster processing and higher-quality processing, but is not necessary for proper operation of the method.

Estimation of Recorded Image Displacement in the Thermogram and the Optical Image While estimating image displacement, keypoints are located in both the thermogram and the optical image. It is desirable for the keypoints to be clearly visible both in the thermogram and the optical image (e.g. sharp edges) and it is desirable for the keypoints to represent the same object or part thereof. By solving the optimization problem in any widely known way (e.g. Descent Gradient, Genetic Algorithm, etc.) the offset is obtained by adjusting the thermogram and the optical image in such a way that the total nonconformity error between corresponding pairs of keypoints become minimal. The nonconformity error may be calculated as an error function representing the distance between corresponding pairs of keypoints in any known or other method (e.g., Root Mean Square Error).

Localization of Inspected Body Part Template Considering a Body Part Outline in the Thermogram and the Optical Image An affine transformation capable of transforming the base body part image to correspond to the inspected body part outline in the thermogram and the optical image is estimated. Transformation parameters (such as scale, rotation, translation, mirror, shear, etc.) may be estimated by solving the optimization problem in any known way (e.g. Descent Gradient, Genetic Algorithm, etc.). Body part templates compliancy may be estimated in any known way of vector line correspondence to line or edge represented in image (e.g. Edge detection etc.). Deformable Templates matching may be used to identify the outline of inspected and contralateral body parts outlines in the thermogram and the optical image.

Fine Tuning of Inspected Body Part Template Considering the Person's Body Part Outline in the Thermogram and the Optical Image During the fine-tuning process, the points of the inspected body part template transformed with affine transformation are matched with the body part outline line or edge to to achieve an optimal fit. However, the anatomical body part shape is preserved by using accumulated reciprocal positions of corresponding points in a previously analyzed body part shape. Thus, the body part shape is obtained by fitting the body part shape on the thermogram and the optical image.

Localization of Contralateral Body Part Template Considering Body Part Outline in the Thermogram and the Optical Image An affine transformation capable of transforming the base body part image to correspond to the contralateral body part outline in the thermogram and the optical image is estimated. Transformation parameters (such as scale, rotation, translation, mirror, shear, etc.) may be estimated by solving the optimization problem in any known way (e.g. Descent Gradient, Genetic Algorithm, etc.). Body part templates compliancy may be estimated in any known way of vector line correspondence to line or edge represented in image (e.g. Edge detection, etc.).

Fine Tuning of Contralateral Body Part Template Considering Body Part Outline in the Thermogram and the Optical Image During the fine tuning process, the points of contralateral body part template transformed with affine transformation are matched with the body part outline line or edge to achieve an optimal fit. However, an anatomical body part shape is preserved by using accumulated reciprocal positions of corresponding points in previously analyzed body part shapes. Thus, the body part shape is obtained by fitting the body part shape on the thermogram and the optical image.

Estimation of Sets of Points of Interest for Both Inspected Body Part and Contralateral Body Part According to the Appropriate Body Part Template The positions of points of interest are estimated by applying affine and non-affine transformations in succession to the base set of points of interest for each body part. Non-affine transformation coefficients are estimated according to the body part template points of the appropriate body part. Additional points laid inside the body part shape polygon may also be used for better transformation preparation.

Estimation of Temperature Maps for Both Inspected Body Part and Contralateral Body Part According to the Appropriate Set of Points of Interest Each value of the temperature maps is estimated by generalizing temperature values situated near the position of points of interest in the thermogram of the appropriate body part. Any known type of temperature values generalization may be used (e.g. mean, median, weighted mean, etc.).

Estimation of Temperature Disparity Map

Estimation of temperature disparity map may be performed by subtracting the temperature values in the temperature map of the contralateral body part from the appropriate temperature values in the temperature map of the inspected body part.

Composition of Set of Inflammation or Functional Disorder Regions

Composition of set of inflammation or functional disorder regions is performed by analyzing the temperature disparity map in order to find the local areas containing temperature disparity values higher than the medically based threshold. Candidate inflammation or functional disorder regions are composed of the nearby points of the temperature disparity map exceeding a medically based threshold. The threshold may be found in medical literature, set by a researcher or doctor, or found via any other method. Descriptive feature vector is created for each candidate inflammation or functional disorder region composed of estimations of generalized values of points, interposition, temperatures, or any combination thereof.

Analysis of Inflammation or Functional Disorder Regions

Analysis of inflammation or functional disorder regions is performed by examining the feature vectors. During this process, non-confident inflammation or functional disorder regions are rejected in order to clear the list against accidentally marked non-inflammable regions (e.g. the area deemed too small, or having a relatively small temperature excess, etc.). For better compliancy any historically accumulated data may be used to perform this task. Any type of classificatory or machine learning functional step may be used to perform this task (e.g. support vector machine, artificial neural network etc.).

Detection of Inflammation or Functional Disorder

Each body part for each human or animal has a threshold for the temperature differences which would signal an inflammation or a functional disorder. The temperature differences are obtained by comparing the differences in thermograms of inspected and contralateral body parts. If an unpaired body part is monitored, the comparison is made between the inspected area and an area adjacent to the unpaired body part (e.g., if an area of the abdomen is monitored, then an adjacent area on the abdomen may be monitored for the comparison). The same inspected body part can be used as a contralateral body part when the data is used from a different thermogram, which was taken previously. If the temperature differences surpass the threshold value, it would indicate inflammation of the body part, and the early onset of inflammation or other functional disorder may be suspected.

Figure 3:
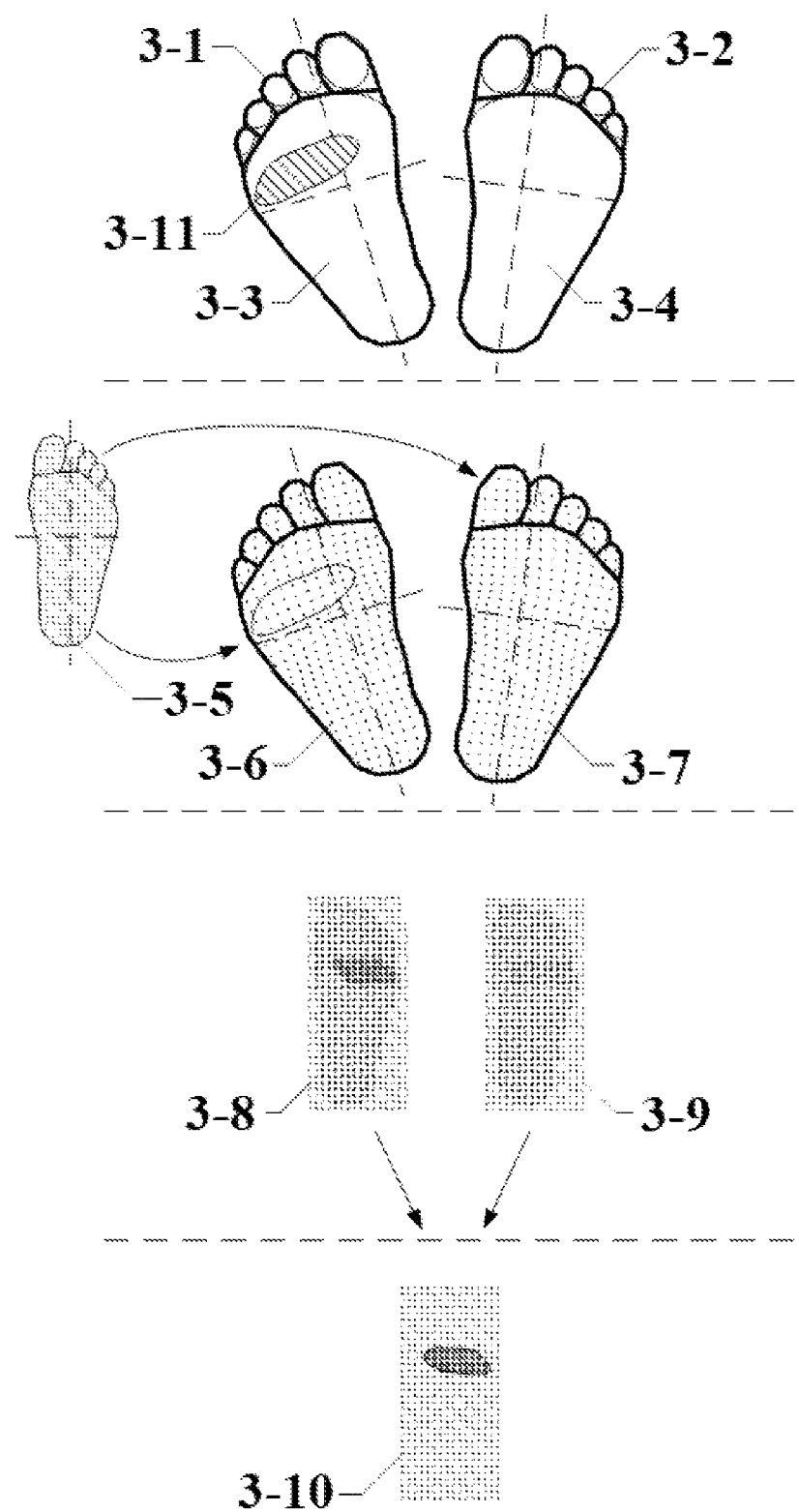
FIG. 3. An example of the principal functional steps of the method, when the body parts are feet. Here: 3-1—Inspected foot with fitted template; 3-2—Contralateral foot with fitted template; 3-3—Inspected foot; 3-4—Contralateral foot; 3-5—Initial template with a grid; 3-6—Inspected foot template with a grid; 3-7—Contralateral foot template with a grid; 3-8—Inspected foot temperature map; 3-9—Contralateral foot temperature map; 3-10—Temperature difference map.

The working principle of the method is presented in FIG. 3, when the method is applied for the inspection of feet. The inspected foot is marked as (3-3), while the contralateral foot is marked as (3-4). After fine tuning of the inspected body part template, the inspected foot with a fitted template is obtained (3-1). The same procedure of fine tuning of the body part template is performed for a contralateral foot, so the contralateral foot with the fitted template is obtained (3-2). 3-5 shows an initial template with a grid. The initial template with the grid (3-5) is applied for both the inspected foot and the reference (contralateral) foot. As a result, the inspected foot template with grid (3-6) and the contralateral foot template with grid (3-7) are obtained. Then the temperature maps for both the inspected foot and the contralateral foot are estimated according to the appropriate set of points of interest. (3-8) shows an inspected foot temperature map and (3-9) shows a contralateral foot temperature map. Estimation of a temperature disparity map is performed by subtracting the temperature values in the reference foot temperature map from the appropriate temperature values in the inspected foot temperature map, and the temperature difference map (i.e., temperature disparity map) (3-10) is obtained. The temperature difference map (3-10) shows the temperature differences between the inspected foot and the contralateral foot, and these temperature differences could be set for different values. If the temperature differences surpass the medically based threshold value, this temperature asymmetry may indicate an inflammation or a functional disorder.

Figure 4:
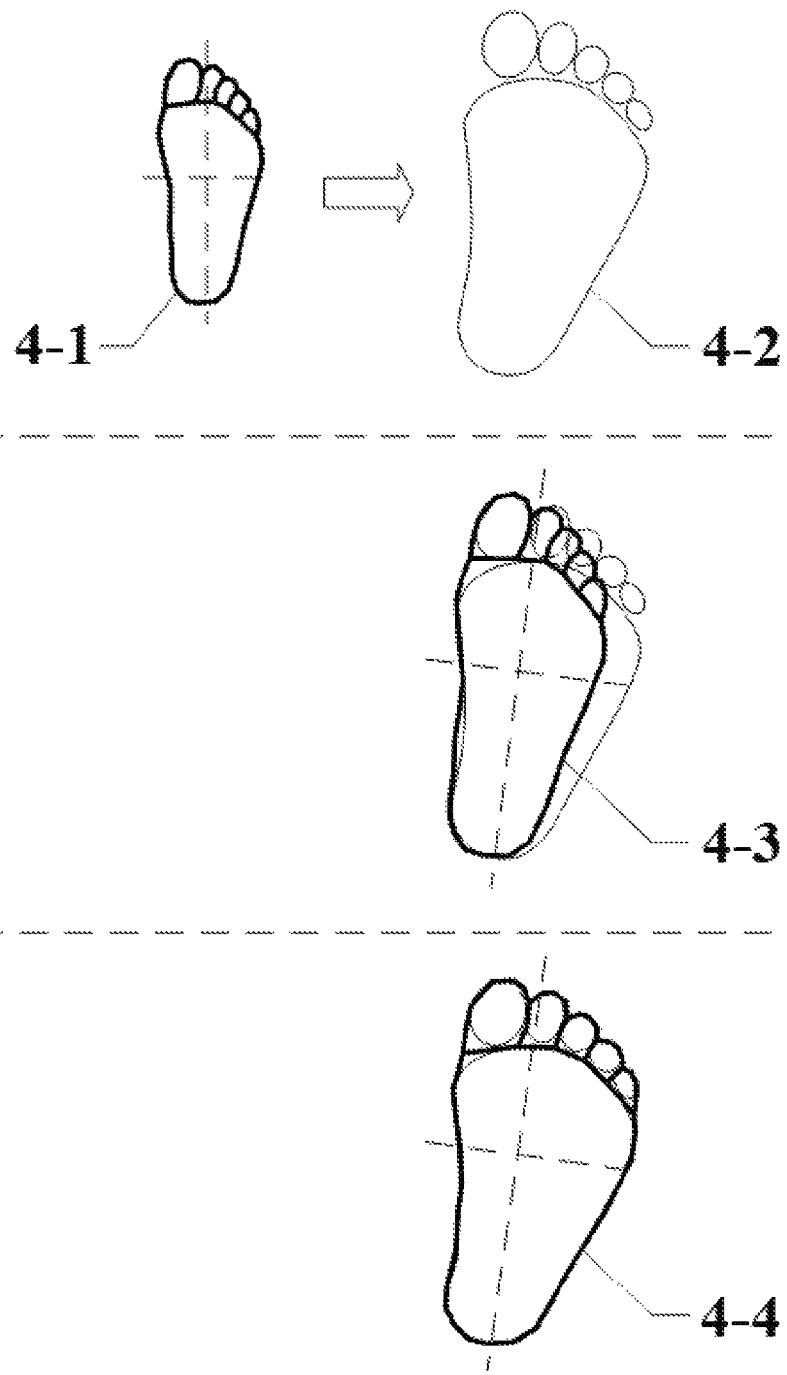
FIG. 4. An example of the template transformation, when the body part of a patient is a foot.

The fine tuning of a foot template in more details is presented in FIG. 4. Here the foot is marked as 4-2 and the foot template is marked as 4-1. Initially, a rigid transformation is performed, and a foot template transformed with rigid transformation is obtained (4-3). This foot template is not accurate, so a non-rigid transformation is performed. After the non-rigid transformation, the accurate foot template is obtained (4-4).

Sending the Data to the Mobile Device (1)

The processing unit (4) sends the data indicating absence of the inflammation or functional disorder to the mobile device (1), where the user is informed about his/her health state. If the system or apparatus is configured in such a way that the data about the user health state could be accessed to his/her healthcare specialist, the data about the user health state is sent to the healthcare specialist of the user. If the temperature differences are below the threshold value, the user and/or his/her healthcare specialist is informed that the signs for the disease or the functional disorder of the inspected body parts were not detected. If the temperature differences surpass the threshold value, the user and/or his/her healthcare specialist is informed about the signs for the early onset of the inflammation or other functional disorder and is advised to visit the healthcare specialist for further examination at the healthcare institution.

The method may be used for automatic detection of inflammation or functional disorder regions. The method is based on temperature asymmetry estimation in inspected and contralateral body parts.

In the preferred embodiment of the present invention, the method is used for inflammation detection in soles of the feet. Diabetic foot wounds or diabetic foot ulcers (DFUs) can be caused by neuropathy and arterial disease in the lower limb. DFUs are difficult to diagnose early, and even more difficult to treat. Thus, an advanced home assessment tool to monitor the feet of people with diabetes is needed. Numerous studies have indicated that local temperature change in the foot is a clear precursor to diabetic foot ulcer. It was determined that a 1.8 degree Fahrenheit (1.8° F.) to 3.6° F. (1° Celsius (c) to 2° C.) temperature increase within the foot, compared to the mean temperature of the contralateral requires an accurate assessment in order to decide whether it is a normal increase or an indication of present or forthcoming foot ulcers. Moreover, temperature differences of more than 3.96° F. (2.2° C.) between a region on one foot and the same region on the contralateral foot may be considered hyperthermia. Monitoring such differences through thermal images captured with the use of infrared thermography devices proves to be an efficient method of detecting diabetic foot ulceration.

The method of monitoring two feet of a human is based on taking the temperature and optical images of both feet simultaneously. The method automatically detects the outline of two feet from the thermal images and enables comparison of the temperature maps of both feet. The method described herein advantageously automatically detects the outline of two feet, eliminates the background and other thermal objects that may be in the background, determines the temperature differences of the feet, localizes the exact area of the temperature differences, and automatically indicates the signs of the inflammation. Finally, the method produces an output message indicating the risk of an ulcer emerging on the foot as a function of whether the temperature map is determined to present the at least one of the prescribed patterns. The medically based threshold is understood to be 3.96° F. (2.2° C.), but any other threshold also may be used and does not limit the process described in this document. The emergence of an ulcer is based on a comparison of both feet in a 'mirror way', identifying temperature differences of 3.96° F. (2.2° C.) or greater on respective areas of the contralateral foot. Additionally, the temperature differences indicative of the ulcer, could be set for different values.

Figure 5:
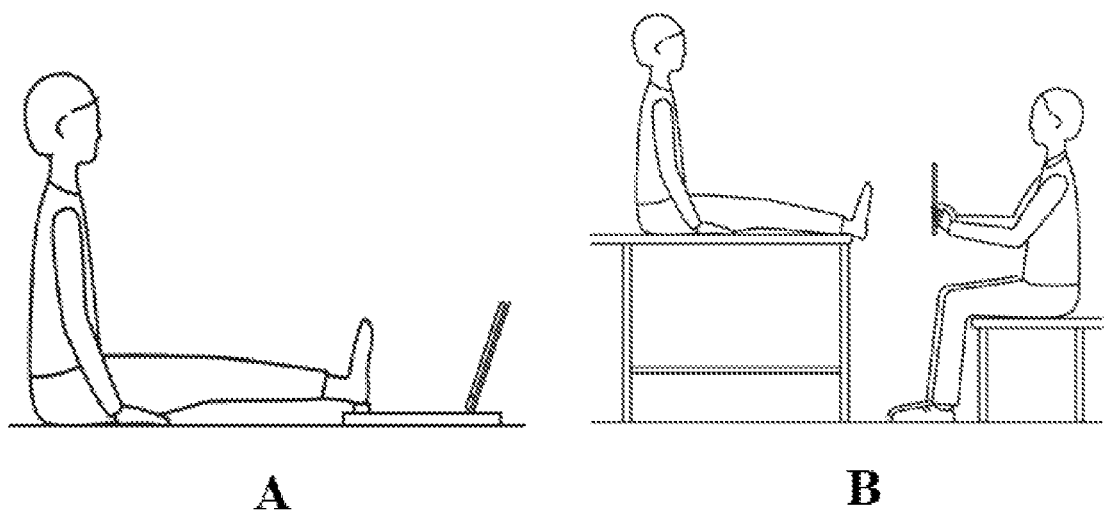
FIG. 5. Different modes of usage of the apparatus. A—the apparatus, being used by the person himself/herself. B—the apparatus, being used by the healthcare assistant.

The apparatus and the method can be used by a person at home, at health care institutions, or at other locations where periodic inspection of feet may be beneficial or necessary. The following figures show how the apparatus can be used by a person self-inspecting his/her feet (FIG. 5A) and having his/her feet inspected by the healthcare assistant (FIG. 5B). The device and the apparatus can be used by a person with diabetes mellitus or other conditions that may result in damaging of the foot. Data about the state of the feet can also be directly transferred to a healthcare specialist who is assigned to monitor the feet or overall health of that person. This notification to the medical professional can be done via an email, phone text message, notification on their software application, or another means of data transfer (which may be encrypted to comply with various medical data regulations). When the person and/or his/her assigned healthcare specialist receives the feedback about the health state of the feet, they can take the appropriate measures to mitigate or prevent complications.

As an example of the apparatus use for the inflammation detection in feet soles, the apparatus could have the following characteristics. During the measurement, the feet are photographed in such a way that they have a length of about 400 pixels and a width of about 160 pixels considering the thermogram resolution 480×640 pixels, so the foot outline may contain 400*160*0.75=48000 pixels. Here 0.75 is a ratio that takes into account the influence of the roundness of the foot on the foot area. Grid of points of interest may be distributed in regular way taking in to account cells size as a division of the length of the identified foot by 100, i.e. the foot grid height is said to be 100 cells. Then the width of the foot would be about 40 cells. Therefore, the foot area will be equal to 100*40·0.75=3000 cells. If the above mentioned foot outline length was 400 pixels, the cell size value will be equal (400/100)^2=16 pixels of the thermal imager (approximately one unit of temperature per square millimeter). This means that 3000*16=48000 points of the thermal imager are involved in the evaluation of the foot. However, lower resolution (generalized data) with 16 values per square centimeter is used for evaluation, so that the cell size is about $2.5^{-3} \times 2.5^{-3}$ mm. In principle, cell size can be reduced even more times while increasing the measurement resolution, but this may increase the probability of false-positive inflammation detection cases, when a change of a temperature of a small area would be treated as a pathology. Selected cell size is relative and may be selected based on the real data for optimal performance.

In another embodiment of the present invention, the method is used for breast cancer thermography. The use of the method is based on the principle that metabolic activity and vascular circulation in both pre-cancerous tissue and the area surrounding a developing breast cancer is almost always higher than in normal breast tissue. In an ever-increasing need for nutrients, cancerous tumors increase circulation to their cells by holding open existing blood vessels or creating new blood vessels. This process frequently results in an increase in regional surface temperatures of the breast. The temperature changes may be among the earliest signs of a pre-cancerous state of the breast. Certain types of cancers will not be detected (approximately 20%) by mammography for various reasons, such as for women who are on hormone replacement, nursing or have fibrocystic, large, dense, or enhanced breasts. These types of breast differences do not cause difficulties in reading minor temperature changes of breast. However, the temperature changes of the healthy and the pre-cancerous tissues are small, thus a method having extreme sensitivity is needed.

The proposed method measures the temperature changes of both breasts simultaneously, thus the temperatures of certain breast parts could be compared. The method automatically detects the outline of two breasts, eliminates background, determines the temperature differences of the breasts, localizes the exact area of the temperature differences, and automatically indicates the signs of the possible pre-cancerous or cancerous tissues. If the temperature differences surpass threshold values (which may be determined based on medical literature), the person may be suggested to consult a healthcare specialist for further diagnosis, and the temperature difference or other related data may be transferred to the healthcare specialist.

In conclusion, the method, described in the proposed invention, provides the following non-limiting advantages:
- It is a non-invasive and non-contact (or minimal contact) body part monitoring method;
- It provides temperature maps of body parts;
- It automatically identifies the temperature changes of body parts, indicating the potential signs of early onset of an inflammation or other functional disorders;
- It automatically detects the outline of body part(s) despite the real world background normally present at home and other indoor and outdoor environments;
- It is user-friendly both for users both at-home and at a healthcare institution;
- It is suitable for people with limited mobility and sight;
- Healthcare assistant or assistance at home is not mandatory for use of device and the method;
- It has a possibility for real-time alerts provided to a healthcare assistant in case of detected temperature increase;
- It informs the user and/or his/her healthcare specialist about the health status and the possible signs of inflammation or other functional disorder; in the former case the person is advised to visit the healthcare specialist.

What is claimed is:

1. A method for an early detection of a diabetic foot ulcer based on temperature asymmetry estimation in feet, the method comprising:
   recording, using an optical camera and a thermal camera, an optical image and a thermogram corresponding to a first foot and an optical image and a thermogram corresponding to a second foot;
   receiving, by a processing unit, the optical image and the thermogram corresponding to the first foot and the optical image and the thermogram corresponding to the second foot;
   estimating, by the processing unit, a recorded image displacement based on the optical image and the thermogram corresponding to the first foot including localizing a template of the first foot on the optical image and on the thermogram corresponding to the first foot by locating corresponding pairs of keypoints in the optical image and in the thermogram corresponding to the first foot, and calculating a nonconformity error between the corresponding pairs of keypoints in the optical image and in the thermogram corresponding to the first foot;
   estimating, by the processing unit, a recorded image displacement based on the optical image and the thermogram corresponding to the second foot; and
   determining, by the processing unit, the early detection of the diabetic foot ulcer in the first foot by comparing the thermogram corresponding to the first foot to the thermogram corresponding to the second foot based on the recorded image displacement corresponding to the first foot and the recorded image displacement corresponding to the second foot.

2. The method of claim 1, wherein estimating the recorded image displacement corresponding to the first foot further includes fine tuning by fitting a shape of the first foot on the optical image and the thermogram corresponding to the first foot.

3. The method of claim 2, wherein estimating the recorded image displacement corresponding to the second foot further includes localizing a reference template of the second foot by locating corresponding pairs of reference keypoints in the optical image and in the thermogram corresponding to the second foot, and calculating a nonconformity error between the corresponding pairs of reference keypoints in the optical image and in the thermogram corresponding to the second foot.

4. The method of claim 3, wherein estimating the recorded image displacement corresponding to the second foot further includes fine tuning by fitting a reference shape of the second foot on the optical image and the thermogram corresponding to the second foot.

5. The method of claim 1, wherein the optical image and the thermogram corresponding to the first foot are recorded simultaneously.

6. The method of claim 1, wherein determining the early detection of the diabetic foot Ulcer in the first foot includes rejecting non-confident inflammation or functional disorder regions.

7. The method of claim 1, wherein determining the early detection of the diabetic foot ulcer in the first foot includes estimating temperature maps for the first foot and estimating temperature maps for the second foot based on the the first foot and based on the thermogram of the second foot.

8. The method of claim 7, wherein comparing the thermogram corresponding to the first foot to the thermogram corresponding to the second foot includes comparing the estimated temperature maps.

9. The method of claim 1, wherein the optical image corresponding to the first foot and the optical image corresponding to the second foot are included in a single optical image taken by the optical camera, and wherein the thermogram corresponding to the first foot and the thermogram corresponding to the second foot are included in a single thermogram taken by the thermal camera.

10. The method of claim 1, wherein the optical image corresponding to the first foot and the optical image corresponding to the second foot are taken sequentially, and wherein the thermogram corresponding to the first foot and the thermogram corresponding to the second foot are taken sequentially.

11. The method of claim 7, wherein determining the early detection of the diabetic foot ulcer in the first foot further includes estimating a temperature difference map being a single map that shows a difference between the estimated temperature maps for the first foot and the second foot.

12. The method of claim 2, further comprising:
estimating, by the processing unit, points of interest for the first foot and for the second foot based on the fine tuning corresponding to the first foot and based on the fine tuning corresponding to the second foot; and
estimating, by the processing unit, temperature maps for the first foot and for the second foot based on the points of interest.

* * * * *